United States Patent [19]

Boos et al.

[11] Patent Number: 4,832,490
[45] Date of Patent: May 23, 1989

[54] PHOTOMETER

[75] Inventors: Michael Boos, Hanau; Werner Klug, Freigericht; Alfons Zöller, Bad Soden-Salmünster, all of Fed. Rep. of Germany

[73] Assignee: Leybold-Heraeus GmbH, Cologne, Fed. Rep. of Germany

[21] Appl. No.: 80,428

[22] Filed: Jul. 31, 1987

[30] Foreign Application Priority Data

Aug. 11, 1986 [DE] Fed. Rep. of Germany ....... 3627232

[51] Int. Cl.[4] ............................................... G01J 3/42
[52] U.S. Cl. ..................................... 356/325; 356/382; 356/434
[58] Field of Search ................................ 356/323-325, 356/326, 328, 381, 382, 432, 433, 434, 436-439, 447, 448; 280/575, 227

[56] References Cited

U.S. PATENT DOCUMENTS 3,270,348  8/1966  Lesage et al. .................... 356/434 X
3,392,623  7/1968  Walker et al. ....................... 356/434
4,305,663  12/1981  Perkins et al. ..................... 356/323
4,661,711  4/1987  Harjunmaa ......................... 356/417

FOREIGN PATENT DOCUMENTS 718434     3/1942  Fed. Rep. of Germany .
2630645    1/1977  Fed. Rep. of Germany .
2631770    1/1978  Fed. Rep. of Germany .
216323A   12/1984  Fed. Rep. of Germany .
3403372    7/1985  Fed. Rep. of Germany .
3406645    8/1985  Fed. Rep. of Germany .
384003     8/1973  U.S.S.R. ........................... 356/448
689856     4/1953  United Kingdom ............... 356/434

Primary Examiner—F. L. Evans
Attorney, Agent, or Firm—Felfe & Lynch

[57] ABSTRACT

A photometer in which a measuring phase, a reference phase and a dark phase are produced by means of a chopper. These phases are staggered in time, so that a single detector can be provided for all phases. In the photometer the object to be measured is situated between two light conductors, the one light conductor leading to the detector and the other light conductor leading to the chopper input. The chopper output is carried by an additional light conductor to the detector.

17 Claims, 6 Drawing Sheets

PHOTOMETER

The invention relates to a photometer having a light source, a detector, a light chopper with at least one chopper disk, and having light conducting means, wherein several first ends of light conducting means together are coupled to the detector and several second ends of light conducting means together face the light source, and wherein the object to be measured is disposed between third ends of light conducting means.

Photometers are widely used for the measurement of light transmission or reflection. One known application of photometers is the measurement of the thickness of coatings deposited from a vapor onto sheets of glass or the like. These coatings are very thin and are of the order of magnitude of wavelengths of light, which makes them difficult to measure.

A multi-channel process spectrometer is known which has an illuminating system, a sensor system and a spectrometer system; the sensor system is connected by a first light conducting fiber to the illuminating system and a second light conducting fiber is connected to the spectrometer system (DE-PS No. 34 03 372). The light coming from the first light conducting fiber passes through a sample that is situated within the sensor system, while the light passing through the sample is received by the second light conducting fiber and transmitted. This spectrometer, however, is a chopper-less single-beam apparatus having a continuous measuring phase.

Also known is an electromechanical light chopper for four different wavelengths, in which the light, after passing through a filter, is conducted by a light conductor cable to the object to be tested (DD-PS No. 216 323). This chopper, however, is not suitable for the production of a reference phase and a dark phase.

Also, a colorimeter is known which has a lamp which emits light in the visible spectrum, which is carried by a light conductor to a sample (DE-OS No. 26 31 770). This colorimeter, however, has to do with a chopperless single-beam apparatus. The filter wheel serves only for changing the wavelength of measurement.

Also known is a spectral photometer system for measuring the optical properties of transparent, reflective and radiating material in relation to light wavelength, especially for measuring the variation of optical properties during the production of thin coatings on substrates in vacuum chambers, and having a spectral light separating system and a series of measuring cells (DE-OS No. 34 06 645). This spectral photometer system is intended to make it possible to test a number of points of measurement and objects which are independent of one another with a single measuring and evaluating system while preserving accuracy. To achieve this aim, each point of measurement is associated with a glass fiber cable, while the glass fiber cables are arranged directly adjacent and parallel to one another. The single object is disposed between the ends of two glass fiber conductors of which one glass fiber conductor is connected to a light source and the other glass fiber conductor is connected to an evaluating system. Although glass fibers are used in this known spectral photometer system, it is not a system based on the chopper principle, but a so-called chopperless single-beam apparatus. The masks associated with the glass fibers can be used only for shifting the points of measurement, not for producing a measuring phase, reference phase and dark phase.

Light conducting fibers are also used in another known photometric analyzer (DE-OS No. 26 30 645). This known analyzing system, however, has to do with a chopped single-beam system with a measuring phase and a dark phase. The reference is formed simultaneously with the measuring phase by a second detector.

A two-beam photometer with a three-phase chopper is also known (U.S. Pat. No. 4,305,663). This two-beam photometer, however, does not have a light conducting system.

Lastly, a push-pull photometer having a light conductor optic is known in which light streams from the sample and the standard of comparison or standard light beam fall in rapid alternation on a photoelectric cell (DE-PS No. 718,434). In this case, for the phasing of the two light beams against one another on the perforated disk, which has a row of holes within a gap in the light conductor optic, the one light conducting system, which is adjustable in the direction of movement of the perforated disk, is provided with light entry and exit surfaces facing the perforated disk and the light conducting optic, respectively. In this known push-pull photometer, the width of the light entry and exit surface is the same as the width of the holes in the perforated disk, while the cross section of the light conductor optic carrying the light beam in and out is larger. Furthermore, the cross section of the standard light beam at the chopping point is matched to the cross section of the adjustable light conducting system for example by diaphragming.

This known push-pull photometer is a two-phase chopper without a dark phase, in which the chopper disk is not disposed between the light source and the light conducting system. The disadvantage which such a photometer entails consists especially in the fact that great light losses are incurred in the coupling of the light to the light conductor.

It is therefore the object of the invention to create a photometer which will have substantially less light loss.

This object is achieved by disposing the light source in a gap in a light conducting system whose one end is opposite the object being measured and whose other end is opposite the detector, and a chopper disk can be introduced at least part of the time.

The advantage achieved with the invention is that, by means of a chopper, a measuring phase, a reference phase and a dark phase can be produced, and these different phases can be staggered in time. Moreover it is possible to perform photometric measurements in a vacuum coating apparatus with a high long-term stability. By the use of light conductors in conjunction with the three phase chopper, a two-beam principle can be achieved in one apparatus. Since the measurement of the measurement light and reference light is performed with the same detector, the light source drift and the detector drift are compensated.

In accordance with the invention, a photometer comprises a light source, a detector, and a light chopper having at least one chopper disk. The photometer also includes light conductor devices having a plurality of first ends of the light conductor devices together facing the detector and having a plurality of second ends of the light conductor devices together facing the light source and having a plurality of third ends of the light conductor devices between which third ends an object to be measured is disposed. One of the light conductor devices having one end facing the object to be measured and one of the light conductor devices having an end facing the detector form a gap in which the light source is disposed and in which at least one of the chopper disks is introduced at least for a time.

For a better understanding of the invention, together with other and further objects thereof, reference is made to the following description, taken in connection with the accompanying drawings, and its scope will be pointed out in the appended claims.

Referring now to the drawings.

Figure 1:
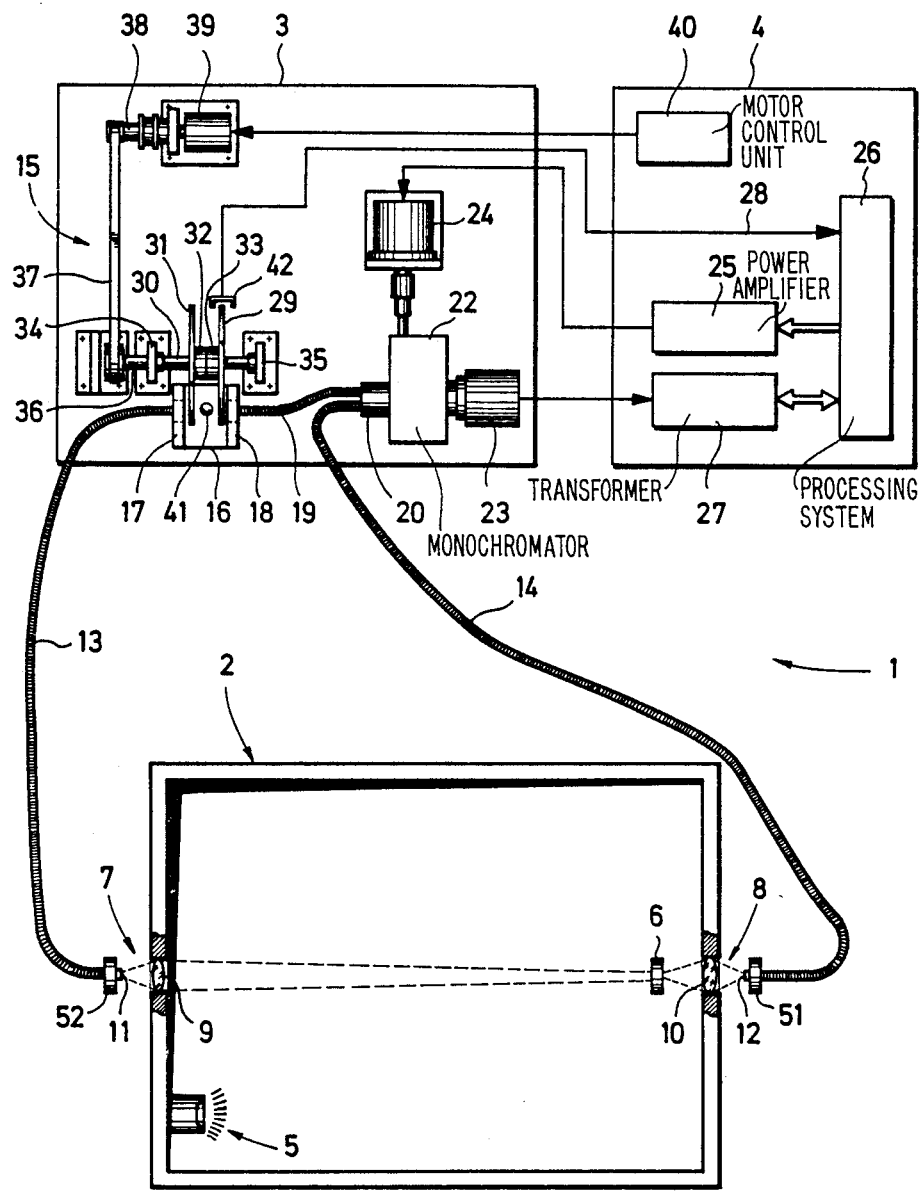
FIG. 1 is representation of an embodiment of a photometer according to the invention.

The basic arrangement of a photometer 1 according to the invention is represented in FIG. 1. This photometer 1 is connected to a measuring chamber and has a measurement converter 3 and a signal processor 4. In the measuring chamber 2, which is, for example, the vacuum chamber of a coating apparatus, is an evaporation source 5 which emits metal or metal oxide vapors which deposit themselves on a test glass 6 or other substrate. This test glass 6 is situated between two orifices 7 and 8 in the measuring chamber 2, these openings being filled each by an optical lens 9 and 10, respectively. Outside of the measuring chamber 2, and at a slight distance from the lenses 9 and 10 are the ends of light conductor clusters 11 and 12 which are encased in flexible metal tubes 13 and 14. The light conductor cluster in the metal tube 13 runs to a chopper system 15. This chopper system consists of a chopper chamber 16 having two walls 17 and 18, the second end of the light conductor cluster in the metal tube 13 being introduced into the one wall 17. On the other hand, a reference light conductor cluster 19 is inserted into the other wall 18 and leads to a cluster coupler 20 which is connected to the light conductor cluster in the metal tube 14. This cluster coupler 20 is connected to a monochromator 22 to which a detector 23 is coupled. A stepping motor 24 is provided for driving gratings or interference filters in the monochromator 22 and is controlled by a power amplifier 25 in the signal processor 4. This power amplifier 25 is in turn controlled by a processing system 26 which, among other things, receives the signals of the detector 33 through a transformer 27. This processing system 26 is fed information from a straddling photodetector 42 through a line 28, which indicates the status of the rotation of a chopper disk 29. This chopper disk 29 is disposed in a shaft 30 on which a second chopper disk 31 is also situated. Tee two chopper disks 29 and 31 are separated from one another by spacers 32 and 33 and are affixed to the shaft 30. The ends of the shaft 30 are journaled in bearings 34 and 35, one end 36 of them being engaged by a drive belt 37 that is driven by a drive shaft 38. This drive shaft 38 is joined to a motor 39 which is driven by a motor control unit 40. Between the two chopper disks 29 and 31 there is provided a lamp 41 which throws light on the reference section and, at another time, on the measuring section.

By means of the system represented in FIG. 1, the absolute reflection or transmission of the layer deposited on the test glass 6 can be measured with a high long-term stability. This is accomplished by the fact that, by means of the chopper disks 29 and 3, a measuring phase, a reference phase and a dark phase are produced. Since here the measuring phase and the reference phase occur at different times, the two phases can be measured with the same detector 23 and at the same wavelength of the monochromator 22. The measuring phase is determined by the light conductor cluster in the metal tube 13 and by the chopper disk 31, while the reference phase is determined by the light conductor cluster in the metal tube 19 and by the chopper disk 29.

During the measuring phase, a portion of the light of lamp 41 is delivered through the light conductor cluster in the metal tube 13 to the lens 9. From the latter it goes to the test glass 6 and through lens 10 into the fiber cluster 12 in the metal tube 14 and into the cluster coupler 20 and from there to the monochromator 22. In the monochromator 22 a certain range of wavelengths of the incoming light is filtered out and fed to the detector 23. The latter converts the optical signal to an electrical signal and delivers it to a transformer 27 which delivers it after appropriate adaptation to the processing system 26.

During the reference phase the light of lamp 41 is released by the chopper disk 29 to the light conductor cluster in the metal tube 19. It then passes also through the cluster coupler 20 to the monochromator 22 and from there it is fed through the detector 23 and the transformer 27 to the processor 26, in the same way as the light in the measuring phase.

In this manner the light of the lamp 41 is, in a first phase, fed in a form attenuated by the coating deposited on the glass plate 6 to the detector 23, while in a second phase the unattenuated light of the lamp 41 is fed to the detector 23. For certain applications the monochromator 22 can be dispensed with. If, however, it is important to determine the wavelength relationship of the transmission or reflection, the monochromator or some other dispersive element is indispensable.

Since the same lamp 41 and the same detector 23 are used in both phases, aging phenomena and drifting of the temperature of the lamp 41 and/or detector 23 will affect both phases equally, i.e., the errors are compensated.

The dark phase serves for the compensation of errors resulting from external light and/or from drifting of electronic amplifiers. The differences between the measuring phase and the dark phase and between the reference phase and the dark phase are therefore evaluated. The ratio between the measuring and reference values thus obtained is therefore an unfalsified measure of the reflection and transmission, respectively, of the coating deposited on the glass plate 6.

The use of the monochromator 22 is preferred especially when the growing optical coating thickness is measured, i.e., when the optical intensity at a certain wavelength follows a certain function.

Figure 2:
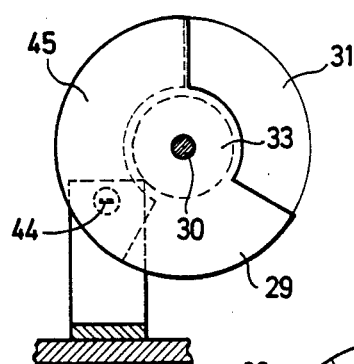
FIG. 2 shows a chopper system in a first position.

In FIG. 2 there is shown a first alignment of the chopper disks 29 and 31. It can be seen that here the chopper disk 29 has a cut-out preferably amounting to about 120° within an outer circle. The end 44 of the glass fiber cluster is shown in broken lines behind the chopper disk 29. The chopper disk 31 likewise has a cut-out preferably of about 120° within an outer circle. This cut-out is situated at the point marked 45. In this alignment the reference light is blocked and the measuring light is released.

Figure 3:
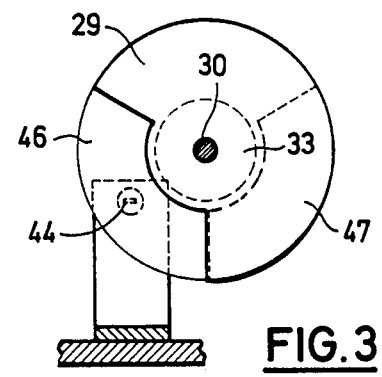
FIG. 3 shows the chopper system of FIG. 2 in a second position.

FIG. 3 shows a second alignment of the chopper disks 29 and 31. The cut-out in chopper disk 29 is in this case at the point marked 46, while the cut-out in the chopper disk 31 is at the point marked 47. In this position the measured value is blocked and the reference value is released.

Figure 4:
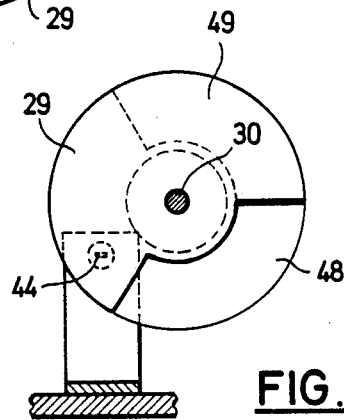
FIG. 4 shows the chopper system of FIG. 2 in a third position.

FIG. 4 represents a third alignment of the chopper disks 29 and 31 in which the cut-out in chopper disk 29 is at point 48. The cut-out in the chopper disk 31, however, is at point 49.

In this case both the measured value and the reference value are blocked, i.e., the dark phase prevails.

Figure 5:
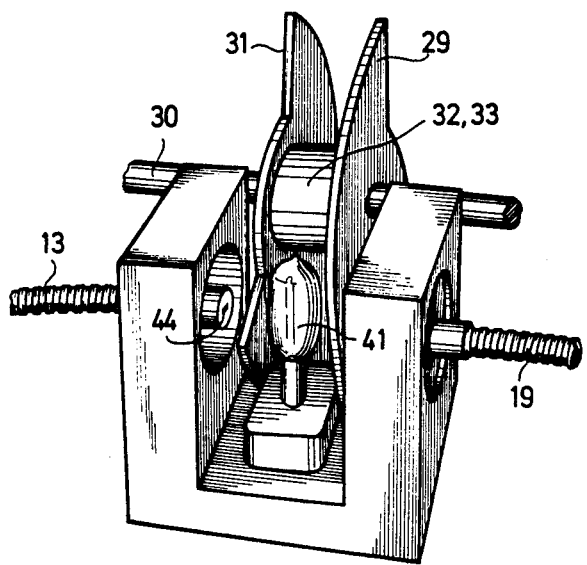
FIG. 5 is a perspective view of the chopper system represented in FIGS. 2 to 4.

FIG. 5 again is a perspective view of the chopper system of FIGS. 2, 3 and 4. Here one sees the ends of the metal tubes 13 and 19, the lamp 41, and the chopper disks 29 and 31. Since the two chopper disks 29 and 31 preferably have cut-outs of 120° which are disposed relative to one another such that they do not overlap, a phase can be reached in which the light of the lamp 41 is blocked off both from the end 44 and from the cluster in the tube 19.

Figure 6:
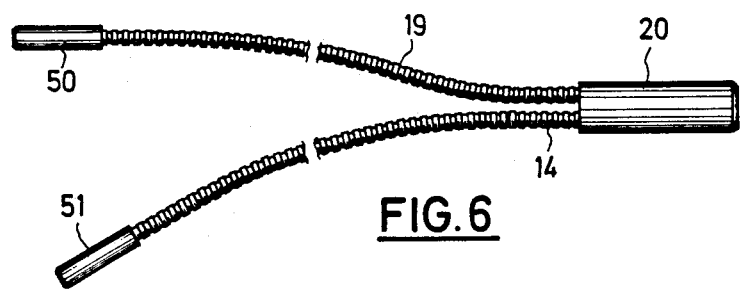
FIG. 6 shows a two-branch light conductor system whose one branch receives the signal from the object and whose other arm contains a reference signal.

FIG. 6 shows a variant of the cluster coupler 20 with the two flexible metal tubes 19 and 14 containing the light-conducting glass fiber clusters.

The ends of the metal tubes 14 and 19 are connected to cylindrical connecting terminals 50 and 51.

Figure 7:
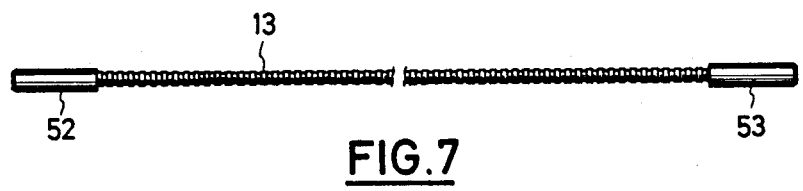
FIG. 7 shows a jacketed light conductor whose one end serves to illuminate the object and whose other end receives chopped light signal.

FIG. 7 shows a metal tube 13 which is provided with cylindrical connecting terminals 52 and 53 at each of its extremities.

Figure 8:
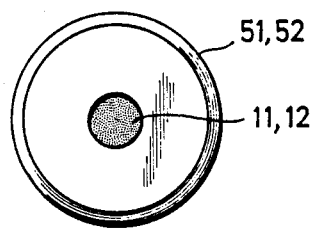
FIG. 8 shows a first end of a light conductor with a circular fiber cluster which receives the light thrown on an object and emits the light coming from the object.

FIG. 8 shows a connecting terminal corresponding to the connecting terminals 51 and 52 in FIGS. 6 and 7, respectively. In these connecting terminals 51 and 52 can be seen the ends of the circular glass fiber clusters 11 and 12.

Figure 9:
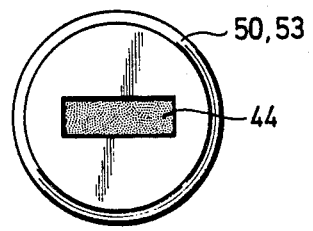
FIG. 9 shows a second end of the light conductor of FIG. 8, with a rectangular cluster of light conducting fibers.

FIG. 9 shows a connecting terminal corresponding to the connecting terminals 50 and 53 in FIGS. 6 and 7. The connecting terminals 50 and 53 shown in FIGS. 6 and 7 do no have to be identical; as a rule, however, they are similar so that both can be represented by the one representation in FIG. 9. The glass fiber cluster 44 here preferably has a rectangular shape which is often advantageous for the coupling of the light output of the lamp and the light conductor. If a halogen lamp is used, the cross section of the light conductor cluster is adapted to the cross section of the lamp filament.

Figure 10:
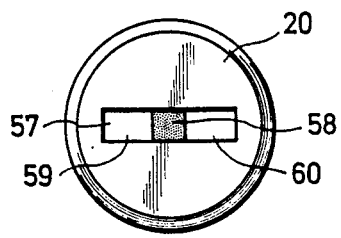
FIG. 10 shows a combination of light conducting fiber clusters in a rectangular cross section in which the middle cluster emits light.

FIG. 10 shows the cluster coupler 20 which has a rectangular slot 57 in which the end of the light conductor fiber cluster 58 is disposed, which is inside of the metal tube 19. On each end of the cluster 58 is half of the cluster 59 and 60, which comes from the connecting terminal 51 (FIG. 6). FIG. 10 is intended to show that only the cluster 58 emits light, while the cluster halves 59 and 60 do not.

Figure 11:
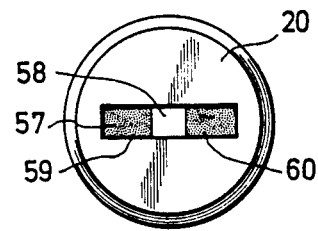
FIG. 11 shows the combination of clusters of light conducting fibers, in which the two outer clusters emit light.
Figure 12:
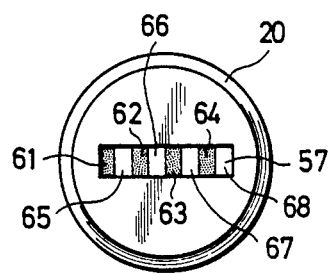
FIG. 12 shows two light conducting fiber clusters divided into smaller clusters set one inside the other, with the smaller clusters of the one light conducting fiber cluster emitting light
Figure 13:
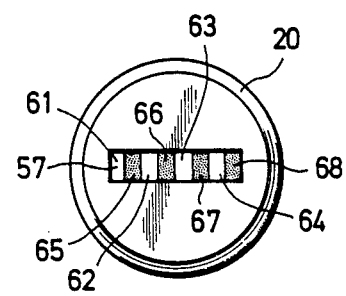
FIG. 13 shows the two light conducting fiber clusters of FIG. 12, in which the smaller clusters of the other clusters emit light.

FIG. 11 differs from FIG. 10 in that now the cluster halves 59 and 60 emit light while cluster 58 is inactive. FIG. 10 therefore shows the reference phase while FIG. 11 shows the measuring phase In FIGS. 12 and 13 two light conductor clusters are shown, which preferably are divided each into four partial clusters 61, 62, 63, 64, and 65, 66, 67, 68, alternating one with the other. In FIG. 12, partial clusters 61-64 emit light while the partial clusters 65-68 are inactive. In FIG. 13, the reverse is the case, and the two light clusters together fill the slot 57.

Figure 14:
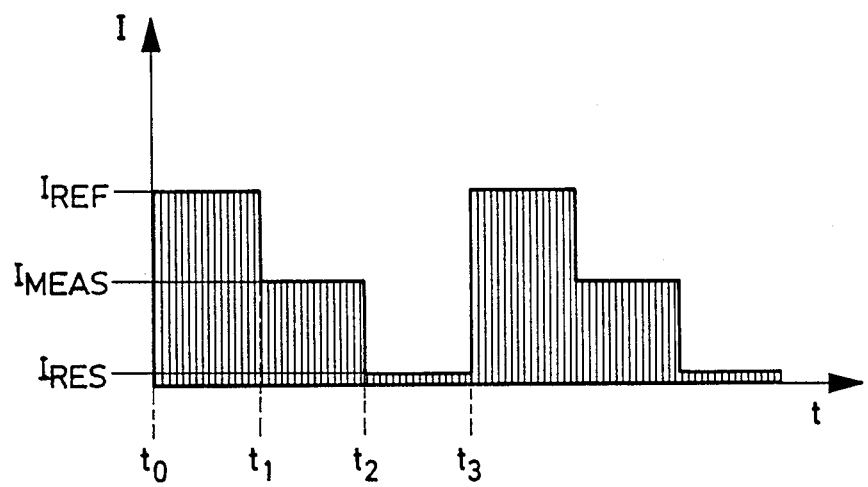
FIG. 14 is a graph indicating the light intensity with respect to time.

In FIG. 14 the light intensity I is represented in relation to time. The light intensity in this case is that detected by the detector 23. Between $t_0$ and $t_1$ the reference signal $I_{REF}$ is detected, which in this example has the greatest amplitude. After that, i.e., between $t_1$ and $t_2$, the measuring signal $I_{MEAS}$ is detected, which is attenuated by the deposit of a material on the plate 6. During the period $t_2$ to $t_3$ the dark phase prevails, so that all that is detected is the residual light strength $I_{RES}$. This residual light can be stray light coming, for example, from the evaporation source 5.

The voltage signal emitted by the detector 23, which can be a silicon element, is digitalized in order then to compare it with I/t curves which have previously been numerically computed, and in order to be able automatically to set the optimum amplification of $I_{REF}$, $I_{MEAS}$, and $I_{RES}$. A high resolution can be achieved by using a voltage-to-frequency converter in the digitalization.

Figure 15:
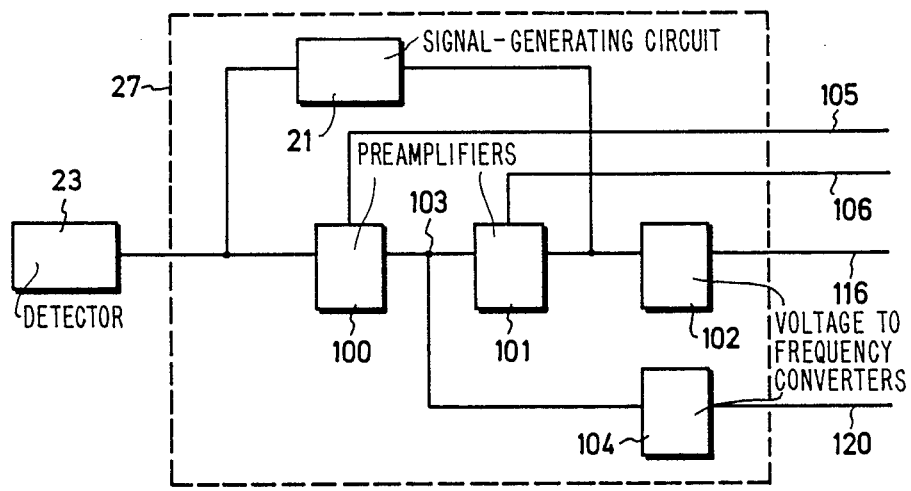
FIG. 15 is a block circuit diagram of a measuring amplifier.

FIG. 15 shows a block circuit diagram of a measuring amplifier 27 for the output signal of the detector 23 by which the voltage is converted to a corresponding frequency. The output of the detector 23 is connected to a first preamplifier 100 whose output is connected to the input of a second preamplifier 101. The output of this second preamplifier is fed to a voltage-to-frequency converter 102 which converts the amplitude of the output voltage of preamplifier 101 to a proportional frequency. Thus, at the output of the voltage-to-frequency converter 102 there is delivered a signal whose frequency corresponds to the measured magnitude.

From the junction 103 between the amplifiers 100 and 101 there is taken a signal which is fed to a voltage-to-frequency converter 104 and converted to a frequency-proportional signal. The amplification of amplifiers 100 and 101 can be set by the processor 26 through the lines 105 and 106, respectively.

Block 21 is a circuit which generates a signal which serves, for example, to compensate overshoots.

Figure 16:
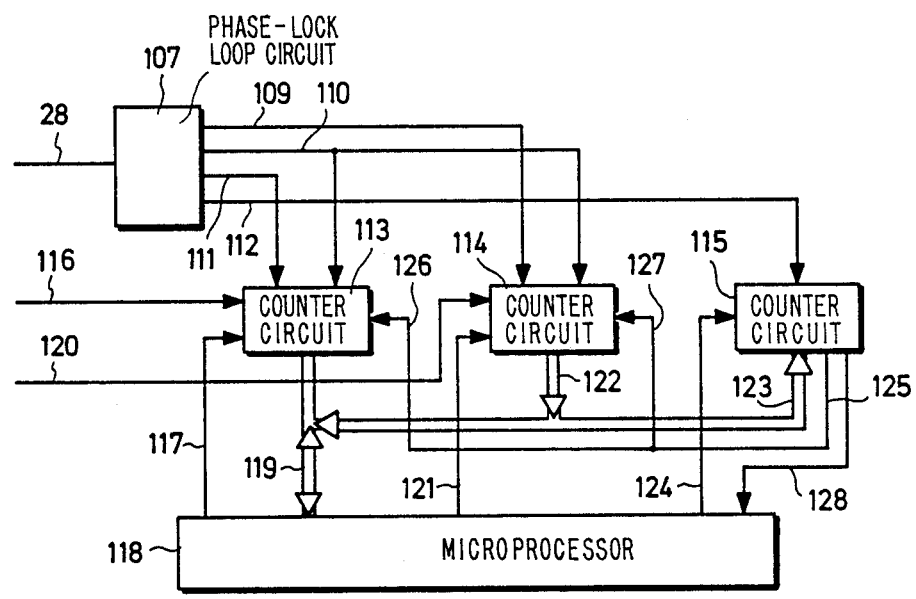
FIG. 16 is a block circuit diagram of a digital, synchronous-phase rectifier.

FIG. 16 shows the block diagram of a lock-in amplifier for three phases. This lock-in amplifier can be part of the processing unit 26. It has a phase-locked loop (PLL) circuit 007 which is fed with a trigger signal from the photodetector 42 of the light chopper. This PLL circuit 107 has four outputs 109, 110, 111 and 112 of which output 109 is the reference phase, output 110 the measuring phase and output 111 the dark phase. Output 112 indicates the end of the chopper phase. The outputs of the PLL circuit 107 are connected with counter circuits 113, 114 and 115, such that the outputs 110 and 111 are connected to the counter 113, outputs 109 and 110 to the counter 114 and output 112 to the counter 115. Counter 113 counts up in the measuring phase and counts down in the dark phase. On the other hand counter 114 counts up in the reference phase and down in the dark phase. Counter 115 counts the chopper revolutions.

The CLOCK (CL) input 116 of the counter 113 receives the output signal of the voltage-to-frequency converter 102. The READ input of the counter 113, however, is connected with an intersection to the microprocessor 118. Between this microprocessor and the counter 113 an exchange of information takes place through the channel 119 during the measuring and dark phases.

An intensity signal is fed to the CL input of counter 114 through a line 120 and it corresponds to the dark current reference signal, i.e., to the output signal at the voltage-to-frequency converter 104. A signal from the processor 118 is fed through line 121 to the READ input of this counter 114. Also, the counter 114 is connected by a channel 122 to the channel 119. A connection to the channels 122 and 119 is also created by a channel 123 to the counter 115. The number of chopper cycles to be measured is programmed through the channel 123. The WRITE input 124 of the counter 115 is connected to the processor 118. The reset inputs 126 and 127 of the counters 113 and 114 are fed from the input 125 of the counter 115. An averaging conductor 128 connects an output of the counter 115 to the processor 118 and indicates when a pre-programmed interval has ended.

Figure 17:
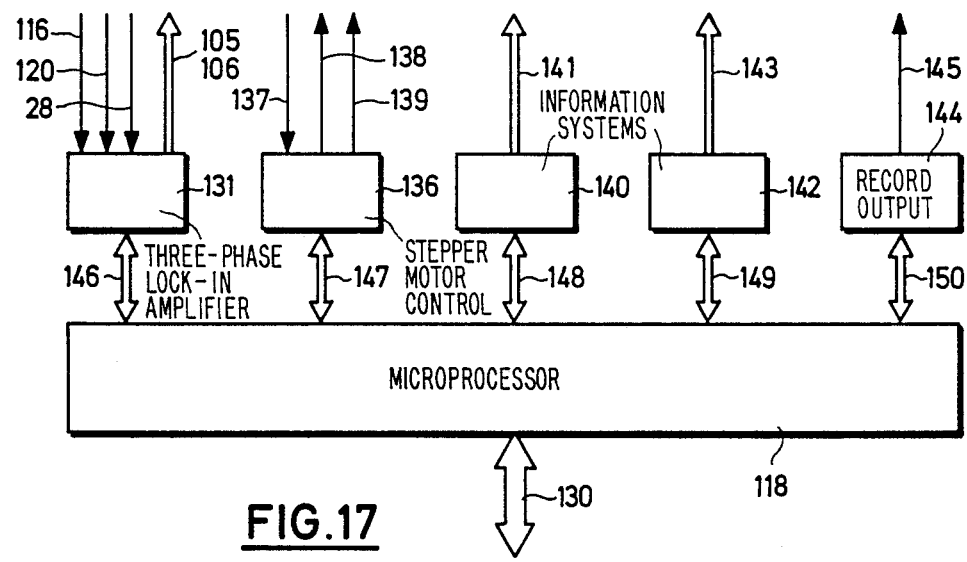
FIG. 17 is an overall block circuit diagram of a microprocessor with different connections.

FIG. 17 is an overall diagram and shows the block circuit of a photometer plate which has a microprocessor 118 with a RAM/EPROM memory which is connected, for example, by a channel 130 to a computer circuit which is not shown. The reference 131 identifies a three-phase lock-in amplifier which corresponds substantially to the arrangement in FIG. 16 and which has three inputs 116, 120, 28 and one output 105, 106. This output 105, 106 contains a signal for an amplification factor.

A stepper motor control 136 has an input 137 and two outputs 138 and 139 which lead to the power amplifier 25. At the input 137 appears a signal from a photodetector in the monochromator 22. This photodetector signal makes possible an automatic calibration of the wavelength of the monochromator 22. This photodetector signal makes possible an automatic calibration of the wavelength of the monochromator 22. The signal for the motor frequency is given by the controller 136 to the line 138. The sense of rotation of this motor, however, is established through the line 139.

The number 140 designates a system into which information can be entered parallel through a channel 141 so as to insert a front plate keyboard. A similar system is provided for the serial entry of information through a channel 143. Lastly, 144 identifies a recording output which is connected by a line 145 to a recording apparatus. All systems 131, 136, 140, 142 and 144 are connected by channels to the microprocessor 118.

Figure 18:
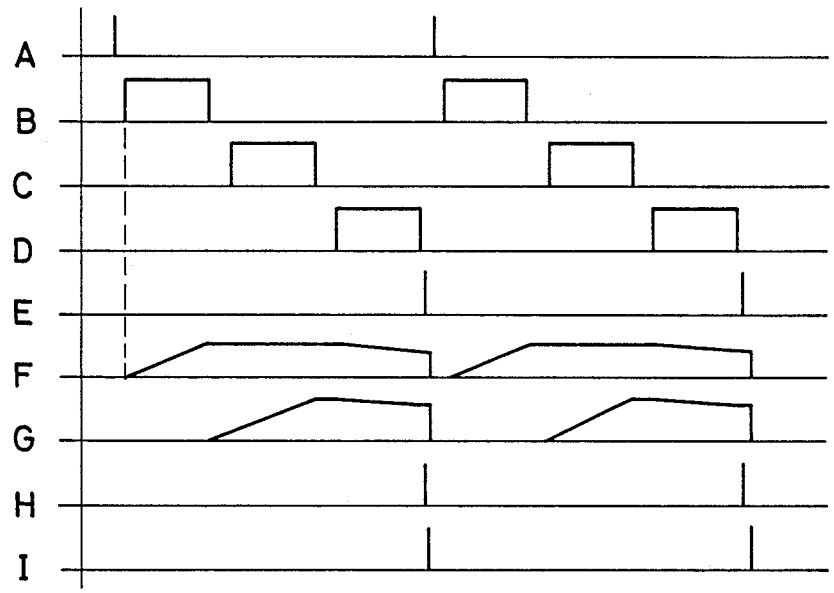
FIG. 18 is a graphic representation of the timing of a digital, synchronous-phase rectifier circuit for three phases.

FIG. 18 is a time diagram of a three-phase lock-in amplifier. The diagram at A constitutes the trigger of the photodetectors (28 and 42 in FIG. 1), while the diagram at B indicates the pulses of the reference phase (109 in FIG. 16). The measuring phase is indicated by the pulses at C (111 in FIG. 16), and the pulses of the dark phase are indicated at D (110 in FIG. 16). The end of the chopper phase is indicated by the pulses at E (112 in FIG. 16), while F indicates the reference signal counter state. The counter state of the measuring signal is represented at G, and the end of the measuring cycle is indicated by the pulses at H. The counter reset pulses are represented in I.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed:

1. A photometer comprising:
   a light source;
   a detector;
   a light chopper having at least on chopper disk having at least one cut-out for light transmission; and
   first, second and third light conductor devices having a plurality of first ends of said second and third light conductor devices together facing said detector and having a plurality of second ends of said first and third light conductor devices together facing of said first and second light conductor devices between which third ends an object to be measured is disposed;
   said first light conductor device having one end facing the object to be measured and said third light conductor device having an end facing the detector forming a gap between said second ends which is coaxial with said first and third light conductor devices adjacent said second ends and in which said light source is disposed and in which at least one of said chopper disks is introduced at least for a time.

2. A photometer according to claim 1, in which said photometer has two chopper disks and in which said light source is disposed between said two chopper disks.

3. A photometer according to claim 2, in which each chopper disk has a cut-out of 120° which does not overlap with the cut-out of each other chopper disk.

4. A photometer according to claim 1, which includes a dispersive element for determining a desired measurement wavelength and for feeding a measuring signal and a reference signal to said detector.

5. A photometer according to claim 4, which includes a drive which moves said dispersive element.

6. A photometer according to claim 2, which includes a motor for driving said chopper disks and which includes controlling means for controlling said motor.

7. A photometer according to claim 1, which includes a processor for evaluating output signals of said 8. A photometer according to claim 5, in which said drive is controlled according to the desired measurement wavelength.

9. A photometer according to claim 1, in which said first, second and third light conductor devices include clusters of light conducting fibers.

10. A photometer according to claim 9, in which two light conducting fiber clusters of said second and third light conductor devices have ends combined spatially such that the total surface area thereof is adapted to a monochromator entry gap.

11. A photometer according to claim 10, in which, for the measurement of the degree of transmission of the object, the object is disposed on a direct line connecting the ends of two of said light conducting devices.

12. A photometer according to claim 10, in which one end of said light conducting fiber cluster of said third light conductor device is situated between one end, split into two halves, of another of said light conducting fiber cluster of said second light conductor device.

13. A photometer according to claim 10, in which one end of light conducting fiber cluster of said third light conductor device is divided into a plurality of partial clusters which are situated between partial clusters of another of said light conducting fiber cluster of said second light conductor device.

14. A photometer according to claim 1, which includes means for digitalizing an analog output signal of the detector.

15. A photometer according to claim 2, which includes counters and in which said chopper disks are so positioned that a measuring phase, a reference phase and a dark phase are detected by means of said counters.

16. A photometer according to claim 1, which includes a memory and in which said detector develops measurement values for comparison with measurement values which are stored in said memory.

17. A photometer comprising:
a light source;
a detector;
a light chopper having at least one chopper disk having at least one cut-out for light transmission; and
first, second and third light conductor devices having a plurality of first ends of said second and third light conductor devices together facing said detector and having a plurality of second ends of said first and third light conductor devices together facing said light source and having a plurality of third ends of said first and second light conductor devices between which third ends an object to be measured is disposed;
said first light conductor device having one end facing the object to be measured and said third light conductor device having an end facing the detector forming a gap between said second ends which is coaxial with said first and third light conductor devices adjacent said second ends and in which said light source is disposed and in which at least one of said chopper disks is introduced at least for a time;
said photometer having two chopper disks and said light source being disposed between said two chopper disks;
and each chopper disk having a cut-out of 120° which does not overlap with the cut-out of each other chopper disk.

* * * * *

UNITED STATES PATENT AND TRADEMARK OFFICE
CERTIFICATE OF CORRECTION

PATENT NO. :    4,832,490
DATED      :    May 23, 1989          Page 1 of 2
INVENTOR(S):    Michael Boos, et al.

It is certified that error appears in the above-identified patent and that said Letters Patent is hereby corrected as shown below:

Column 3, line 24 for "chopped" read -- a chopped --.

Column 3, line 57 for "measuring chamber" read

-- measuring chamber 2 --.

Column 4, line 17 for "detector 33" read

-- detector 23 --.

Column 4, line 22 for "Tee" read -- The --.

Column 4, line 36 for "disks 29 and 3" read

-- disks 29 and 31 --.

Column 6, line 4 for "do no" read -- do not --.

Column 8, line 37 after "facing" insert

-- said light source and having a plurality of third ends --.

Column 8, line 65 after "said" and before the period "." insert -- detector --.

Column 9, line 9 for "10" read -- 1 --.

UNITED STATES PATENT AND TRADEMARK OFFICE
CERTIFICATE OF CORRECTION

PATENT NO. : 4,832,490
DATED : May 23, 1989
INVENTOR(S) : Michael Boos, et al

It is certified that error appears in the above-identified patent and that said Letters Patent is hereby corrected as shown below:

Column 9, line 19 for "end" of light" read

--end of said light --.

Signed and Sealed this

Twenty-third Day of October, 1990

Attest:

HARRY F. MANBECK, JR.

*Attesting Officer*   *Commissioner of Patents and Trademarks*